United States Patent [19]
Tybinkowski et al.

[11] Patent Number: 5,982,844
[45] Date of Patent: Nov. 9, 1999

[54] COMPUTED TOMOGRAPHY SCANNER DRIVE SYSTEM AND BEARING

[75] Inventors: Andrew P. Tybinkowski, Boxford; Michael J. Duffy, Methuen; Gilbert W. McKenna, Revere, all of Mass.

[73] Assignee: Analogic Corporation, Peabody, Mass.

[21] Appl. No.: 08/948,930

[22] Filed: Oct. 10, 1997

[51] Int. Cl.⁶ .................................................. G01N 23/00
[52] U.S. Cl. .................................................. 378/4; 378/20
[58] Field of Search .................................. 378/4–20

[56] References Cited

U.S. PATENT DOCUMENTS

| | | | |
|---|---|---|---|
| 4,093,863 | 6/1978 | Zacher | 378/11 |
| 4,200,799 | 4/1980 | Saito | 378/13 |
| 4,797,008 | 1/1989 | Helbig et al. | 384/49 |
| 5,071,264 | 12/1991 | Franke et al. | 384/501 |
| 5,448,608 | 9/1995 | Swain et al. | 378/4 |

*Primary Examiner*—Craig E. Church
*Attorney, Agent, or Firm*—Lappin & Kusmer LLP

[57] ABSTRACT

In an improved computed tomography scanner drive system and bearing configuration, a gantry disk is sheaved about its perimeter such that the gantry is operable as a driven pulley rotatable about an object to be scanned. A motor assembly mounted to a stationary frame includes a similar sheaved drive pulley. A belt tensioned between the drive pulley of the motor assembly and the driven pulley of the gantry disk transfers rotational motion of the motor to drive the gantry rotationally about the object. In a preferred embodiment, the belt comprises a V-belt or poly-V-belt, and the bearing comprises a wire bearing located proximal to the gantry center of mass. In this manner, the present invention provides a simple and effective technique for driving the gantry about the object, providing sufficiently accurate angular positioning in a reliable and cost effective drive system.

22 Claims, 7 Drawing Sheets

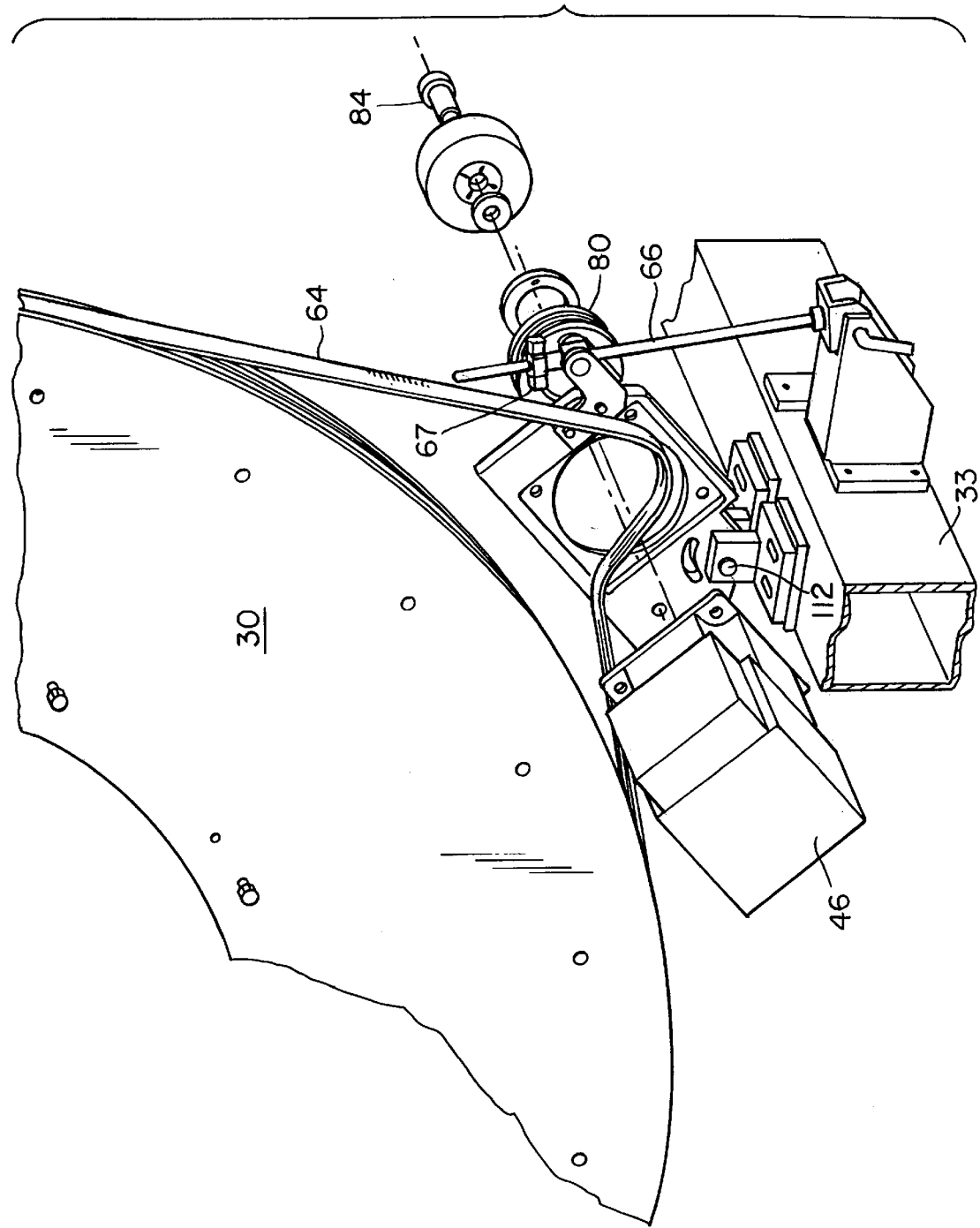

COMPUTED TOMOGRAPHY SCANNER DRIVE SYSTEM AND BEARING

RELATED APPLICATIONS

This application is related to the following U.S. applications filed on even date herewith, of common assignee, the contents of which are incorporated herein in their entirety by reference:

"Air Calibration Scan for Computed Tomography Scanner with Obstructing Objects," invented by David A. Schafer, et al., (Ser. No. 08/,948,937);

"Computed Tomography Scanning Apparatus and Method With Temperature Compensation for Dark Current Offsets," invented by Christopher C. Ruth, et al., (Ser. No. 08/948,928);

"Computed Tomography Scanning Target Detection Using Non-Parallel Slices," invented by Christopher C. Ruth, et al., (U.S. Pat. No. 5,909,477);

"Computed Tomography Scanning Target Detection Using Target Surface Normals," invented by Christopher C. Ruth, et al., (U.S. Pat. No. 5,901,198);

"Parallel Processing Architecture for Computed Tomography Scanning System Using Non-Parallel Slices," invented by Christopher C. Ruth, et al., (U.S. Pat. No. 5,887,047);

"Computed Tomography Scanning Apparatus and Method Generating Parallel Projections Using Non-Parallel Slices," invented by Christopher C. Ruth, et al., (U.S. Pat. No. 5,881,122);

"Computed Tomography Scanning Apparatus and Method Using Adaptive Reconstruction Window," invented by Bernard M. Gordon, et al., (Ser. No. 08/949,127);

"Area Detector Array for Computed Tomography Scanning System," invented by David A. Schafer, et al., (Ser. No. 08/948,450);

"Closed Loop Air Conditioning System for a Computed Tomography Scanner," invented by Eric Bailey, et al., (Ser. No. 08/948,692);

"Measurement and Control System for Controlling System Functions as a Function of Rotational Parameters of a Rotating Device," invented by Geoffrey A. Legg, et al., (Ser. No. 08/948,493);

"Rotary Energy Shield for Computed Tomography Scanner," invented by Andrew P. Tybinkowski, et al., (Ser. No. 08/948,698).

BACKGROUND OF THE INVENTION

In modern third generation computed tomography (CT) scanners, an X-ray source and detector array rotate about a subject or object to be scanned. During a scan, the source and detectors image the object at incremental scan angles. A process referred to as reconstruction generates a series of two-dimensional images or slices of the object from the captured data.

The source, detectors, and related components are mounted to a rotatable gantry supported by a rigid stationary frame. As the gantry rotates, a conveyor passing through a central aperture in the gantry translates the object relative to the sensors. In a fixed system, the object remains fixed during each scan; in a translational or "helical" system, the object continuously translates during the scan. In both fixed and translational systems, precision in the angular velocity, or rotation rate, of the gantry is essential for minimization of reconstruction errors.

Timing belts, or cog belts, have been employed in the past to effect a high degree of precision in rotation rate. A standard timing belt is driven by a motor mounted to the stationary frame. Periodic lateral grooves transverse to the major axis of the belt mesh with teeth on a drive sprocket at the motor and a large driven sprocket mounted to the gantry disk. The driven sprocket must be large enough to avoid interference with the central aperture of the gantry and thus allow room for a object to pass therethrough. For this reason, extraordinarily-large timing belts are required in these systems.

A typical prior art scanner requires at least a six meter timing belt. Timing belts of such a large magnitude are very expensive, as they are difficult to manufacture and often must be custom built, and/or purchased in large quantities. Furthermore, the large driven sprockets are specialized and are therefore expensive, available at a cost of $4,000 to $6,000, depending on the diameter. Alignment between the drive sprocket and driven sprocket must be accurate to a high degree of precision, to avoid lateral walking of the belt relative to the sprockets. Timing belts tend to wear rapidly, and therefore must be replaced frequently, for example once per year for a medical scanner. Replacement is an involved procedure, requiring removal of the scanner system from operation for an extended period of time; perhaps a couple of days. This is due to the fact that in prior art configurations, the driven sprocket is positioned between the annular gantry and the fixed frame. Access to the timing belt for its removal and replacement therefore requires complete removal of the gantry from the frame. Positioning of the sprocket on the component side of the gantry is impractical, since the timing belt would interfere with the rotating gantry components.

A further disadvantage of timing belts in CT systems is their tendency to modulate the rotational speed of the gantry at the frequency of their teeth or cogs. The modulation causes artifacts in the resulting images which must be resolved or otherwise corrected by the image processing system.

SUMMARY OF THE INVENTION

The present invention is directed to a CT scanner drive assembly which mitigates and/or eliminates the shortcomings associated with prior art scanner drive assemblies described above. The apparatus of the invention comprises an annulus, preferably in the form of a disk, which is sheaved about its perimeter such that the annulus is operable as a driven pulley rotatable about an object to be scanned. Electronics are mounted to the annulus for performing a tomographic scan of the object. A motor includes a similarly sheaved drive pulley. A belt tensioned between the drive pulley of the motor and the driven pulley of the annulus transfers rotational motion of the motor to the annulus for driving the annulus rotationally about the object during a scan.

In a preferred embodiment, the belt comprises a V-belt or poly-V-belt. An adjustable tensioner draws the motor drive pulley toward or away from the annulus for adjusting the tension of the belt. The annulus preferably comprises a disk having first and second faces. By spacing the disk from the frame, gantry components may be mounted on both faces of the disk, or through apertures in the disk, mitigating space limitations for mounting components to the disk, and balancing the disk center of mass near the disk plane.

A disk bearing is preferably located at or near the disk center of mass, and mounted to spacers rigidly coupled to the system frame. This configuration reduces the moment arm between the bearing and disk center of mass, improving the life of the bearing and allowing for use of less expensive, simpler bearings, for example Franke four-wire bearings of the type described in U.S. Pat. No. 5,071,264, incorporated herein by reference.

In this manner, the present invention provides a simple and effective technique for driving the annulus about the object to be scanned. The V-belts provide accurate timing—as they minimize slippage, and maximize efficient energy transfer. Further, V-belts offer the additional benefit of a long life time, on the order of five years, before replacement is necessary. Large V-belts are available commercially at a relatively low cost of approximately $100.

This configuration is well adapted for continuous operation in an airport setting for baggage scanning applications and systems which run continuously for 18–20 hours daily. By conveniently locating the belt on an outer edge of the annulus or disk, maintenance of the belt is relatively straightforward and can be performed expeditiously, on the order of 1–2 hours, without the need for disassembling the entire gantry as in the prior art. In addition, V-belts are generally relatively flexible and can be mounted without the need for critical alignment tolerances of prior art timing belts. The flexibility of the V-belt, in combination with its longitudinal grooves provide a smooth interface for driving the disk in continuous motion, without modulating the rotational speed. The drive system therefore makes no contribution to image artifacts.

BRIEF DESCRIPTION OF THE DRAWINGS

The foregoing and other objects, features and advantages of the invention will be apparent from the more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 6A and 6B are exploded perspective views of alternative embodiments of the motor and drive pulley tensioner apparatus in accordance with the present invention.

DETAILED DESCRIPTION OF PREFERRED EMBODIMENTS

Figure 1:
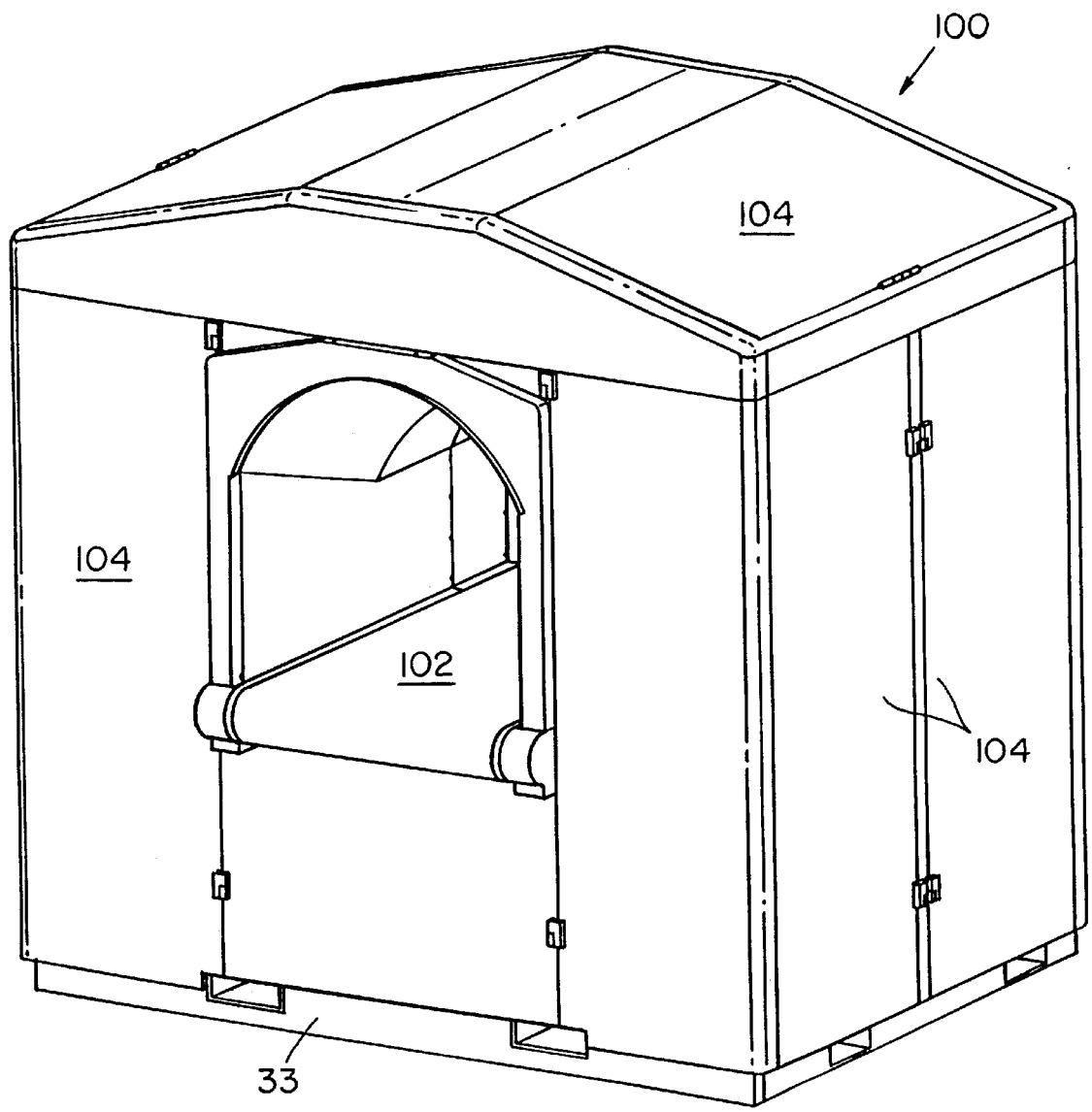
FIG. 1 is a perspective view of an outer console of a computed tomography baggage scanner system in accordance with the present invention.

FIG. 1 is a perspective illustration of an X-ray computed tomography (CT) baggage scanning system outer console 100. The console 100 comprises a plurality of panels 104 mounted to a rigid frame (see FIGS. 2 and 3) erected on a base 33. The panels 104 are hinged to the frame or are otherwise removable to provide access to the inner components of the scanner. A conveyor 102 transports objects to be scanned, for example a human subject or airport baggage, into the scanning area.

Figure 2:
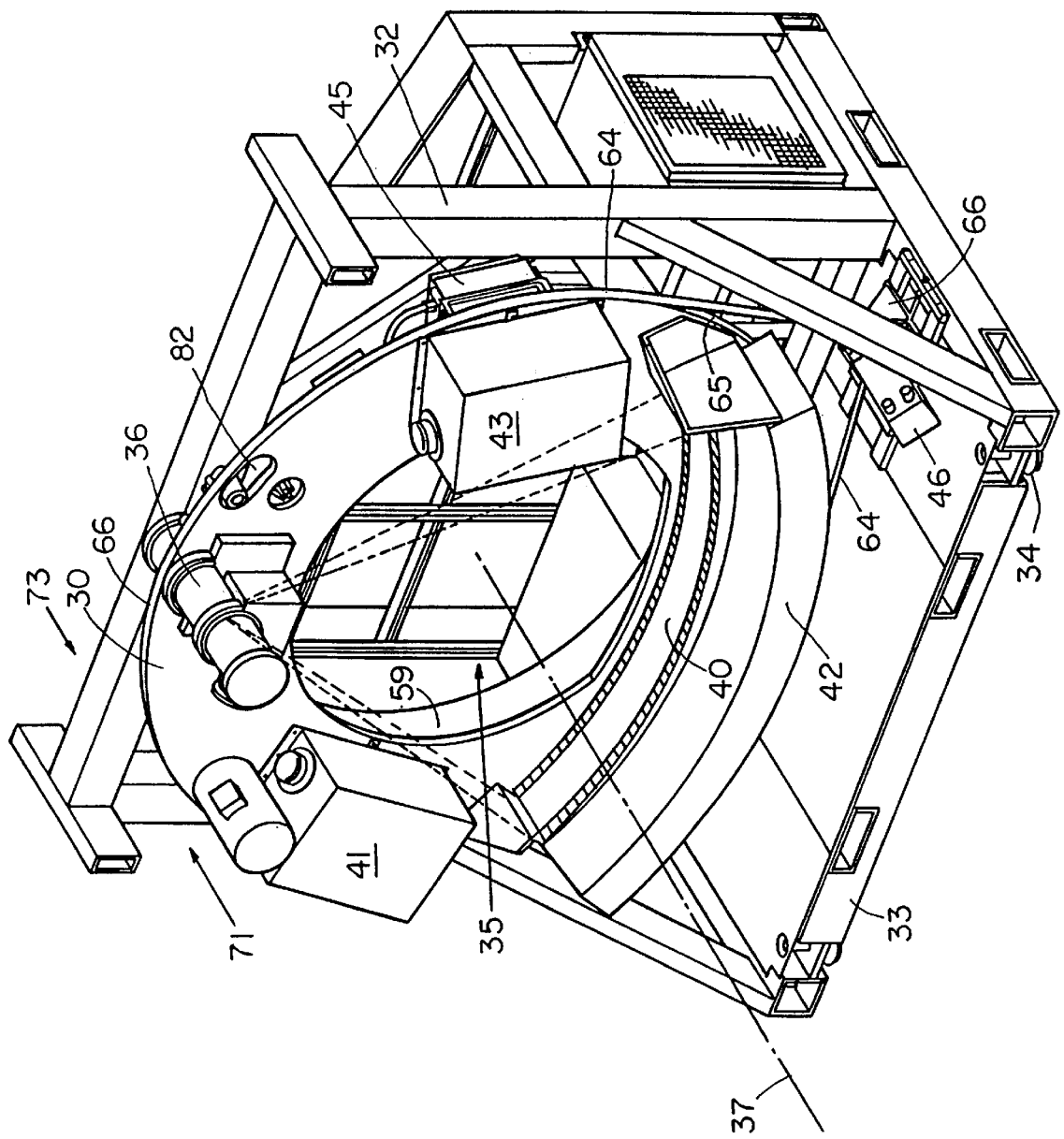
FIG. 2 is a front perspective view of a scanner frame and gantry disk configuration in accordance with the present invention.

FIG. 2 is a front perspective view of the primary components of a CT scanner in accordance with the present invention. A rigid vertical frame 32 is erected on a base 33. The base 33 includes a plurality of height-adjustable feet 34 for leveling the system.

An annulus or disk 30 preferably formed of a lightweight, rigid material such as aluminum, magnesium-aluminum alloy or the like is rotatably mounted on the frame 32. The annulus 30 may be solid or hollow, preferably substantially uniform in cross-section and mass throughout, and is generally radially symmetrical, preferably in the shape of a disk or drum. To ensure that the grain or crystal structure of the disk is structurally uniform, it is preferred that the disk be formed by a precision casting as a single unit, annealed and finished by machining.

An X-ray source tube or source 36 is positioned on the disk 30 for directing an X-ray beam along the plane of the disk 30 across aperture 35 substantially perpendicular to the axis of rotation 37. Similarly, an X-ray detector array 40 is mounted on the disk 30 opposite the source 36 for detecting emitted X-rays 38. Additional components, for example, a data acquisition system 42 for the detector array 40, X-ray power supply cathode 41 and anode 43, air conditioning or cooling systems 45 and related electronics are likewise mounted on both front and rear faces 71, 73 of the gantry disk 30. The disk 30 is rotatably mounted to the vertical frame 32 at bearing 59, the details of which are described below.

A motor 46 and an associated drive pulley 80 (see FIGS. 6A and 6B) coupled thereto drive a belt 64. The belt 64 in turn is coupled to the outer perimeter of the gantry disk 30 for rotating the disk which operates as a driven pulley. The belt 64 preferably comprises a V-belt, for example a poly-V-belt, to confer various advantages described throughout the specification, including low cost, increased longevity, and reduced sensitivity to alignment. Such belts are commercially available from various vendors, for example Browning Inc., Gates Inc., Goodyear Inc., and Jason Inc.

The outer edge 65 of the disk 30 is sheaved to interface with the longitudinal grooves of the poly-V-belt 64. The cross-sectional V-shaped geometry of the belt in combination with the large disk circumference serve to minimize belt slippage, maximizing accuracy in rotational disk positioning and rotation rate. Tension in the belt 64 is controlled by tensioner 66 which adjusts the distance between the motor drive disk 80 (see FIG. 6) and driven pulley 30. Replacement of the belt in this configuration simply involves loosening of the belt 64 at tensioner 66 and removal and replacement of the belt 64 at the front face 71 of the disk. Removal of the disk 30 from frame 32 is unnecessary for belt service in the present configuration, and therefore the belt can be removed and replaced in a matter of minutes.

FIG. 6A is an exploded perspective view of a motor and drive pulley system and corresponding belt tensioner in accordance with the present invention. The motor 46 is coupled to the base 33 at pivot 112. A taper bushing 84 mounts a drive sheave to the motor axle. A tensioner 66 mounted to the motor plate and adjustable by nut 67 adjusts the distance between the drive pulley 80 and the gantry disk 30, thereby adjusting the tension of the belt 64. The tensioner 66 is threaded such that tightening of the nut 67 relative to rod causes the motor 46 to pivot away from the gantry disk 30 thereby tensioning the belt 64. For removing the belt 64 during servicing, the nut 67 is loosened, removing tension in the belt which can thereafter easily be removed at the front face of the gantry disk 30.

Figure 6B:
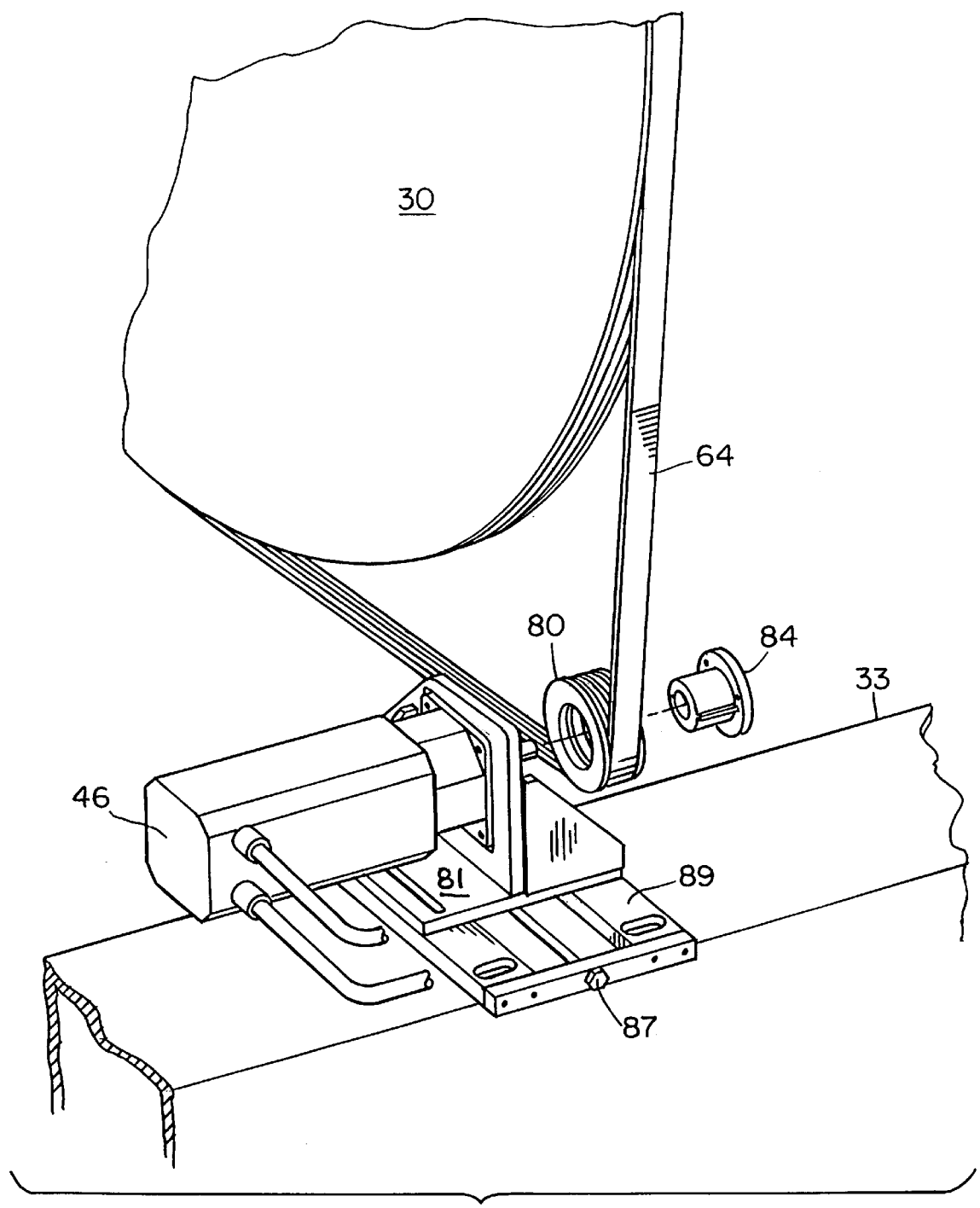

FIG. 6B is a perspective view of an alternative belt tensioner configuration. In this embodiment, the motor 46 is mounted to a movable plate 81 which slides relative to a fixed plate 89. A tension bolt 87 is adjustable for moving the motor 46 relative to the gantry disk 30, thereby tensioning the belt 64.

Figure 3:
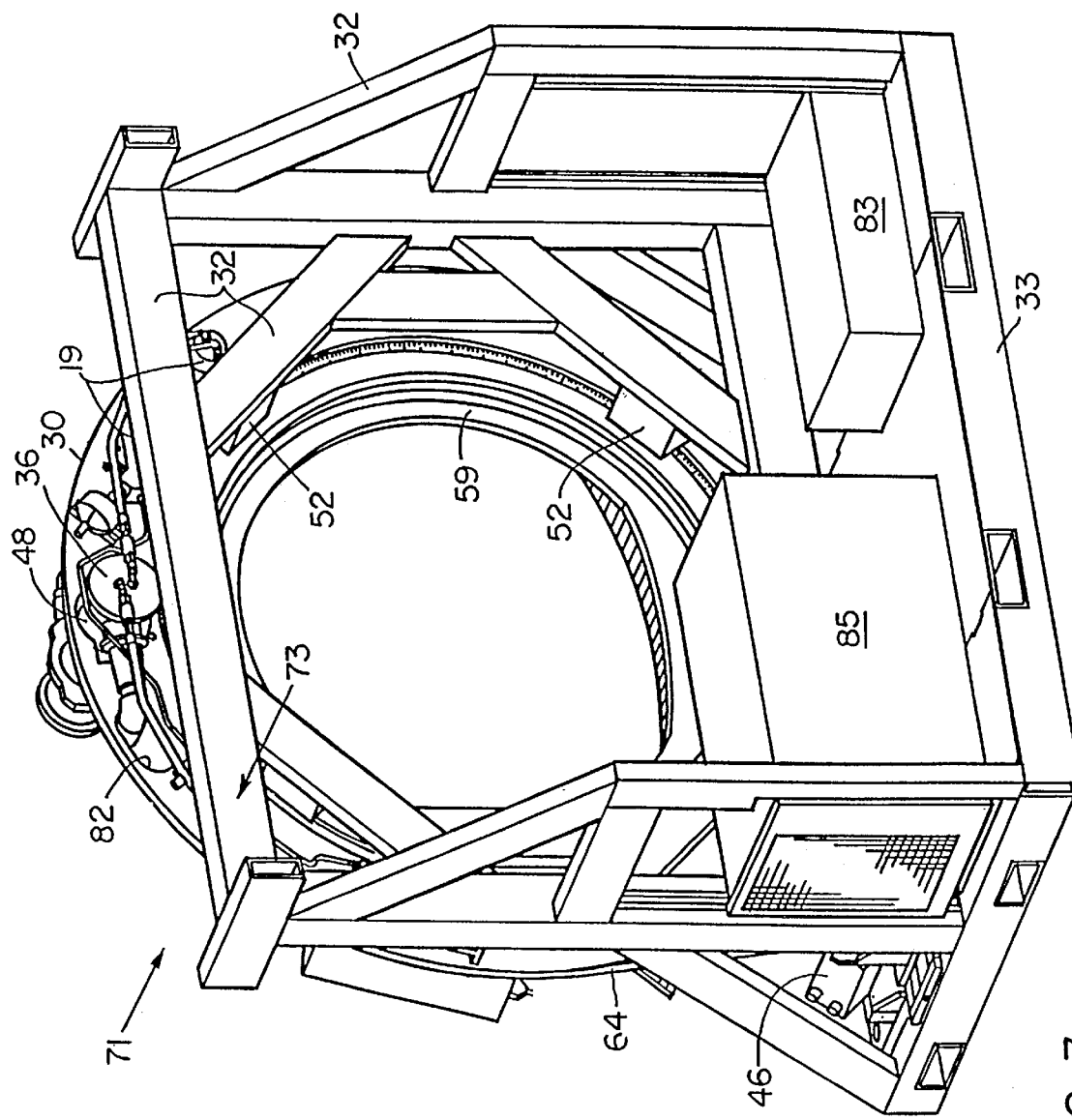
FIG. 3 is a rear perspective view of the frame and gantry disk configuration of FIG. 2 in accordance with the present invention.

FIG. 3 is a rear perspective view of the gantry disk 30 and frame 32. Gantry components mounted on the rear face 73 of the gantry disk 30 are visible in this view, for example, the rear portion of X-ray source 36, and associated cooling systems 19, along with power distribution assemblies, communication units, oil pumps, etc., hidden from view. To provide room for rotation of the rear-face components between the gantry disk 30 and the frame 32, bearing 59 is distanced from the vertical frame by frame spacers or extenders 52. Apertures 82 are provided in the gantry disk 30 to allow for mounting of components through the disk; for example X-ray source 36 passes through aperture 48 and extends from both disk faces 71, 73. Additional apertures 82 allow for passage of signals, power cables, and cooling fluids between components on opposite faces of the gantry disk 30.

Slip rings and corresponding brushes (not shown) transmit power signals and high-bandwidth data signals between components of the gantry disk 30 and frame 32. Microwave transmitter/receiver pairs provide further communication of low-bandwidth control signals. The signals are transmitted to a processing unit 83 which converts the signals to images. Air conditioner system 45 provides for circulation of air and maintains system temperature.

Figure 4:
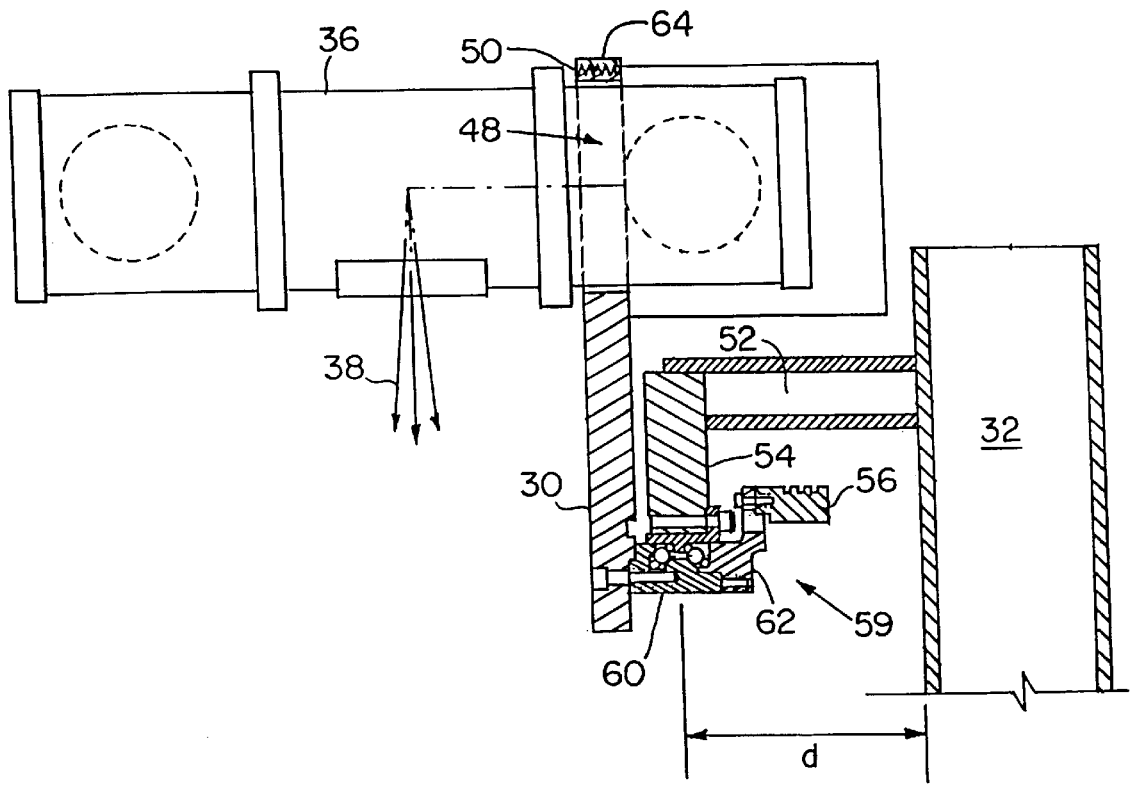
FIG. 4 is a side cross-sectional view of a portion of the gantry and frame of FIGS. 2 and 3, illustrating the sheaved outer edge of the gantry disk and a preferred bearing configuration in accordance with the present invention.

FIG. 4 is a sectional side view of the relationship of the gantry disk 30, bearing 59, and vertical frame 32. The vertical frame 32 supports the gantry 30 system in an upright position, substantially perpendicular to the floor. Frame spacers, or extenders 52 relocate the position of the gantry bearing 59 a distance d from the frame 32 such that the various gantry components are mountable on the rear face of the gantry disk 30 without interfering with the vertical frame 32 during disk rotation. Ring frame 54 serves as a mount for the bearing 59.

Figure 7:
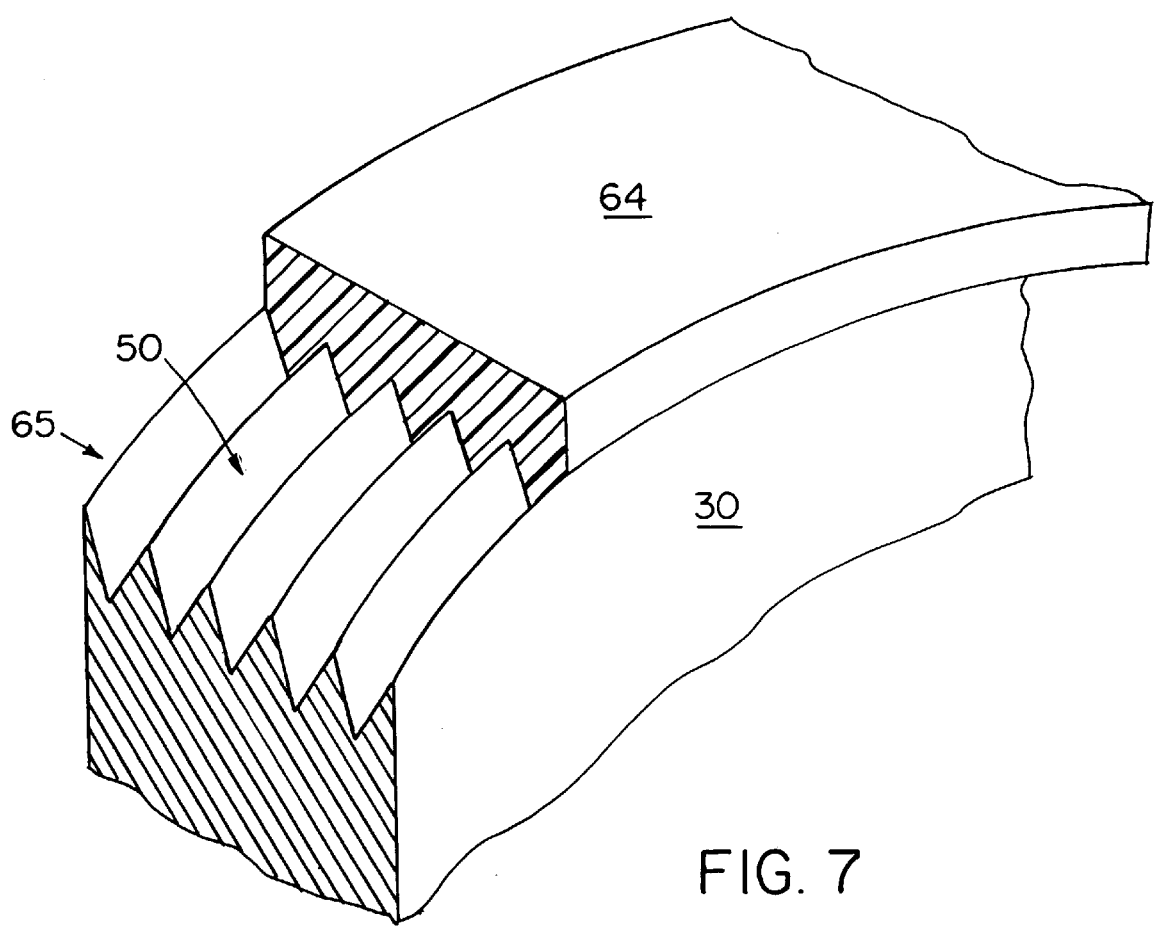
FIG. 7 is a close-up perspective view of the interface between the V-belt and the sheaved outer perimeter of the gantry disk in accordance with the present invention.

The interface between the longitudinal sheaves 50 on the outer perimeter of the gantry disk 30 and the mating longitudinal grooves on the poly-V-belt 64 is visible in the side view of FIG. 4. A close-up perspective view of this interface is shown in FIG. 7. The poly-V-belt and sheave configuration serves to increase the surface area of the interface, thereby minimizing belt slippage.

Although the respective positions of the spacers 52 and bearing 59 could be reversed, with the spacers 52 mounted on the gantry disk 30 surface, and the bearing 59 mounted to the vertical frame 32, such a configuration would increase the moment arm between the bearing and the center of mass of the disk, thereby increasing the radial load and trust load on the bearing. This would require a more robust and therefore more expensive bearing unit. By locating the bearing 59 near or at the center of mass of the gantry, the present invention allows for use of an inexpensive bearing configuration. This, in combination with the mounting of components on both sides of the gantry disk 30, achieves dynamic balancing of the disk relative to the bearing, and reduces the cantilevered load on the bearing.

Figure 5:
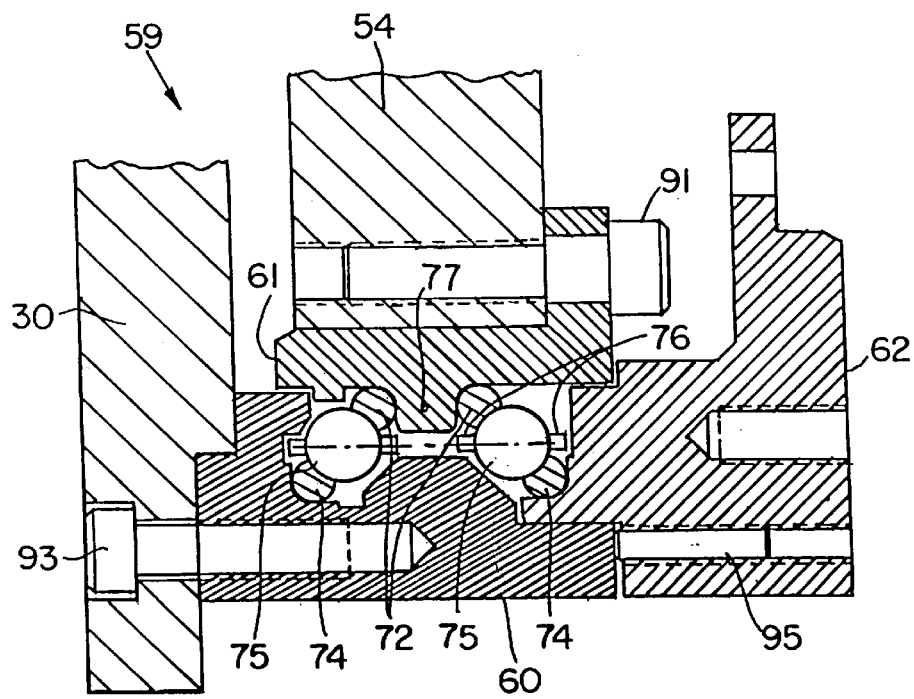
FIG. 5 is a close-up cut-away side view of the improved preferred bearing configuration of the present invention.

FIG. 5 is a close-up sectional view of the interface of bearing 59, which is preferably configured to emulate the well-known Franke bearing interface, as disclosed in U.S. Pat. Nos. 4,797,008 and 5,071,264, incorporated herein by reference. A fixed outer bearing housing 61 mounts to the ring frame 54 by bolts 91. Outer bearing wires 72 are deposited on each inside corner of bearing lip 77, which serves to separate the bearing runs. An inner bearing housing, including first and second inner rings 60, 62 respectively, mounts to the gantry disk 30 by bolts 93. The inner housing includes inner bearing wires 74 laid along the outer corners of the inner bearing housing as illustrated. Suspended between the outer and inner wire races, 72, 74 are spherical ball bearings 75, which glide across the wires with minimal resistance as the gantry disk 30 rotates. Side separators or ball spacers 76 prevent adjacent balls from contacting or otherwise interfering with each other. Preloading of the bearings is controlled by preload bolts 95.

The bearing configuration of the present invention confers several advantages. The bearing/wire interface operates with less friction than traditional bearing races as the wires provide a smooth and efficient track for the bearings. No custom bearing housing is required, as the housing is provided by the inner surfaces of the races. The present bearing configuration requires 10 ft-lbs. of turing torque as opposed to the less efficient prior art designs requiring 50 ft-lbs. of turning torque, assuming a gantry disk of 6 feet in diameter, weighing 1500 lbs, allowing use of a smaller motor, for example a 0.5 horsepower, for rotating the gantry. Furthermore, this bearing configuration is light weight, operates quietly, and is relatively inexpensive.

In an experimental apparatus, the gantry disk comprised a 6 ft. diameter aluminum disk weighing 1500 lbs. A commercially available poly-V-belt having 5 grooves, and commercially available at a cost of $150, was sufficient for rotating the gantry at 90 RPM, using a 1.5 horsepower motor, and delivering an angular rate accuracy better than 0.1%, exceeding the angular rate precision required for accurate scanning.

While this invention has been particularly shown and described with references to preferred embodiments thereof, it will be understood by those skilled in the art that various changes in form and details may be made therein without departing from the spirit and scope of the invention as defined by the appended claims. For example, while the embodiment shown in the drawings illustrates a CT scanner of the third generation type, the invention can be used in CT scanners of the fourth generation type.

We claim:

1. A computed tomography scanning system comprising:
   an annulus having a central aperture for receiving an object to be scanned, said annulus having a sheaved outermost edge such that the annulus is operable as a driven pulley rotatable about said object;
   electronics mounted to said annulus for performing a tomographic scan of said object;
   a motor having a sheaved drive pulley; and
   a belt mounted between said drive pulley and said driven pulley for transferring rotational motion of said motor to said annulus for directly driving said edge of said annulus in rotational motion about said object during a tomographic scan.

2. The system of claim 1 wherein the belt comprises a V-belt.

3. The system of claim 2 wherein the V-belt is a poly-V-belt.

4. The system of claim 1 further comprising a tensioner for adjusting the tension of the belt.

5. The system of claim 1 wherein the annulus sheave is embedded in the outer perimeter of the annulus.

6. The system of claim 1 wherein the annulus comprises a disk having first and second faces.

7. The system of claim 6 wherein said electronics are mounted on both first and second faces of said disk.

8. The system of claim 7 wherein said disk further includes component apertures such that said electronics can be mounted through said disk.

9. The system of claim 1 further comprising a bearing rotationally supporting said annulus.

10. The system of claim 9 wherein said bearing comprises a four-wire bearing.

11. The system of claim 9 wherein said bearing is located proximal to the annulus center of mass.

12. A computed tomography scanning system comprising:
- an annulus having a central aperture for receiving an object to be scanned, said annulus having a sheaved outer edge such that the annulus is operable as a driven pulley rotatable about said object;
- a four-wire bearing rotationally supporting said annulus;
- electronics mounted to said annulus for performing a tomographic scan of said object;
- a motor having a sheaved drive pulley; and
- a belt mounted between said drive pulley and said driven pulley for transferring rotational motion of said motor to said annulus for driving said annulus in rotational motion about said object during a tomographic scan.

13. A computed tomography scanning system comprising:
- an annulus having a central aperture for receiving an object to be scanned, said annulus having a sheaved surface such that the annulus is operable as a driven pulley rotatable about said object; said sheaved surface of said driven pulley having a diameter substantially the same as said annulus diameter;
- electronics mounted to said annulus for performing a tomographic scan of said object;
- a motor having a sheaved drive pulley; and
- a belt mounted between said drive pulley and said driven pulley for transferring rotational motion of said motor to said annulus for driving said sheaved surface of said annulus in rotational motion about said object during a tomographic scan.

14. The system of claim 13 wherein the belt comprises a V-belt.

15. The system of claim 14 wherein the V-belt is a poly-V-belt.

16. The system of claim 13 wherein the annulus sheave is embedded in the outer perimeter of the annulus.

17. The system of claim 13 wherein the annulus comprises a disk having first and second faces.

18. The system of claim 17 wherein said electronics are mounted on both first and second faces of said disk.

19. The system of claim 18 wherein said disk further includes component apertures such that said electronics can be mounted through said disk.

20. The system of claim 13 further comprising a bearing rotationally supporting said annulus.

21. The system of claim 20 wherein said bearing comprises a four-wire bearing.

22. The system of claim 20 wherein said bearing is located proximal to the annulus center of mass.

* * * * *